United States Patent [19]

Sidhu

[11] Patent Number: 4,963,353

[45] Date of Patent: Oct. 16, 1990

[54] METHOD FOR PREPARING A BIOLOGICAL EXTRACT FOR REGENERATING THE HAIR AND SKIN, AND APPARATUS FOR PERFORMING THE METHOD

[76] Inventor: Trilochan S. Sidhu, Adam-Vogt-Strasse 8, D-8910, Landsberg/Lech, Fed. Rep. of Germany

[21] Appl. No.: 306,642

[22] Filed: Feb. 3, 1989

[51] Int. Cl.$^5$ .................. A61K 7/06; A61K 7/075; A61K 7/48; A61K 35/84

[52] U.S. Cl. .................. 424/74; 424/195.1; 47/1.1; 514/783; 252/DIG. 13

[58] Field of Search ............... 424/70, 74, 195.1, 104; 514/738; 435/911, 254; 252/DIG. 13; 47/1.1

[56] References Cited

FOREIGN PATENT DOCUMENTS

| | | |
|---|---|---|
| 0033164 | 6/1981 | European Pat. Off. . |
| 1007957 | 3/1957 | Fed. Rep. of Germany . |
| 1492193 | 11/1969 | Fed. Rep. of Germany . |
| 1617857 | 4/1971 | Fed. Rep. of Germany . |
| 2540971 | 3/1977 | Fed. Rep. of Germany . |
| 2649846 | 5/1978 | Fed. Rep. of Germany . |
| 3039281 | 10/1981 | Fed. Rep. of Germany . |
| 3242446 | 5/1984 | Fed. Rep. of Germany ........ 424/74 |
| 1594884 | 7/1970 | France ................................ 424/74 |

Primary Examiner—Merrell C. Cashion, Jr.
Assistant Examiner—Susan S. Rucker
Attorney, Agent, or Firm—Frishauf, Holtz, Goodman & Woodward

[57] ABSTRACT

A method is disclosed for preparing a biological extract from comminuted fungus material and insect larvae for regenerating the hair and skin. The starting material is held for a relatively long period of time in a vessel provided with a drain device, and the drainage is collected via a collecting tray and then allowed to stand for relatively long periods of time. Finally, the extract is made up with an oil compatible with the skin or an alcohol compatible with the skin to make the desired hair tinctures or skin oils. The preparations are biologically based and served to regenerate hair growth and regenerate and tighten the skin.

18 Claims, 2 Drawing Sheets

METHOD FOR PREPARING A BIOLOGICAL EXTRACT FOR REGENERATING THE HAIR AND SKIN, AND APPARATUS FOR PERFORMING THE METHOD

The present invention relates to a method for preparing a biological extract for regenerating the hair and skin, to the product thus prepared, and to an apparatus for performing the method.

BACKGROUND

The growth of the hair and aging of the skin are causally related to the hormone balance of the body. Hair loss happens primarily to men, but sometimes to women as well, after major changes in the hormone balance, for instance after pregnancy or after treatment with certain medicines.

Numerous preparations and many sources in the literature for means for regenerating the hair and skin are known. Such agents, for promoting hair growth or tightening the skin, are usually based on alcohols or oils and can be roughly divided into three groups, depending on the active ingredients they contain:

(1) Hormones, in particular steroids, such as testosterone, in accordance with German Pat. No. 16 17 857; combinations of estrogens and progestogens in accordance with European Pat. application No. 33 164; human placenta lactogen in accordance with German Pat. Disclosure Document DE-OS 25 40 971.

(2) Vitamins such as biotin (vitamin H), pantothenic acid (vitamin B5) and similar compounds, such as choline and betaine, in accordance with Examined German application No. DE-AS 1 007 957.

(3) Agents which promote blood flow to the scalp, such as horse chestnut extract, in accordance with German Pat. Disclosure Document No. DE-OS 14 92 193; horseradish extract and extract of mustard seeds in accordance with German Pat. Disclosure Document No. DE-OS 30 39 281; alcohol extracts of capsicum in accordance with German Pat. Disclosure Document No. DE-OS 26 49 846; and similar material Other known agents are extract of burning nettles, birch sap, cholesterol and the like, although given the great number of proposals that have been made, the above list cannot be complete According to what is now known (see K. Schrader, *Grundlagen und Rezepturen der Cosmetica* [*Cosmetics: Fundamentals and Formulations*], 1979), although certain successes are attained with agents containing hormones, nevertheless side effects occur in the long term.

Merely looking at the German patent literature alone, it would seem that all hair problems have been solved to complete satisfaction. However, the professional literature in the field and those suffering from these problems express precisely the opposite view. Both the professional literature and the sufferers agree that no reliable agent for regenerating hair growth and for regenerating the skin exists. The agents still used up to now with some success contain steroids, which have serious long-term side-effects.

An effective biological agent for regenerating the hair and skin is also described in German Pat. No. 32 42 446. This is an extract based on skin-compatible alcohols or oils as agents for extracting from a mixture of non-toxic basidia fungi and insect larvae that feed on fungi typically the receptacles of the fungi, which are the above ground or visible portions of mushrooms, for example mushroom heads, as well as their products of metabolism. A method for preparing this agent is also disclosed. However, it has been found that, according to the information given there, the preparation of an effective agent that is of constant quality and always has a high content of active ingredients is not assured in all cases.

THE INVENTION

Accordingly, it is the object of the present invention to provide a method for preparing a biological agent which brings about regeneration of the hair roots and of the skin and thereby effects a fundamental activation of hair growth and skin, in which a high and constant concentration of the active ingredients is attained Briefly, the method for preparing a biological extract for regenerating the hair and skin includes the following steps: (1) a mixture of comminuted receptacles of non-toxic Basidiomycetes and insect larvae that feed on fungi is left to stand for a period of several hours to several days in a container perforated at the bottom, and the liquid composition draining off is collected and conducted into a collecting vessel; (2) from the collecting vessel, this composition is carried to a vessel that is closable in an airtight manner, in which it is left to stand closed for from 2 to 5 days, until a dark-brown color and an intense odor develop, whereupon (3) a skin-compatible alcohol is added in a quantity sufficient to kill the larvae, and (4) the composition is then left to stand, closed, for from 6 to 15 months and preferably from 9 to 12 months, and (5), then the liquid is separated from the sludge material and made up either with a skin-compatible alcohol or a skin-compatible oil.

The invention will be described below in conjunction with the drawings.

DETAILED DESCRIPTION

With the new method, extracts are obtained that show an effect when used on the scalp or on aged skin after as soon as 3 to 4 weeks, and with which hair growth resumes after about 6 weeks. The regenerating action of the agent is particularly apparent because the hair growth resumes virtually in its original color.

As a starting material for the extract to be prepared, the receptacles of non-toxic Basidiomycetes are used. As known, such fungi are composed of an underground mycelium, which produces the receptacles above ground — the visible mushrooms — bearing the spores. Virtually all types and classes of non-toxic Basidiomycetes can be used, but it is favorable to use the fungal receptacles of the Agaricales and/or Boletales and/or Cantharellaceae families. The following types proved particularly favorable: Agaricus, Russula, Xerocomus and Armillariella. Because of their accessibility and excellent suitability, Xerocomus badius or Armillariella mellea or Cantharellus cibarius are particularly preferred.

The second starting material for the extract according to the invention is insect larvae that feed on fungi. Preferably, these insect larvae comprise fly larvae, and the fly larvae of the families Lycoriidae (Sciaridae)

and/or Fungivoridae (Mycetophilidae) are particularly preferred.

The method for preparing the agent begins with well-developed receptacles of the above types of fungus, which are mixed with the larvae, in particular the Sciaridae and/or Mycetophilidae. As a rule, the fungi already exhibit some infestation by such larvae, and such fungi are preferably used. It is also possible, for instance, for cultures of these larvae strongly developed on Armillariella can also be transferred to less-infested receptacles, or colonies of fly larvae developed in suitable media, such as leaves, can be transferred to the receptacles, which favorably are reduced in size.

Figure 1:
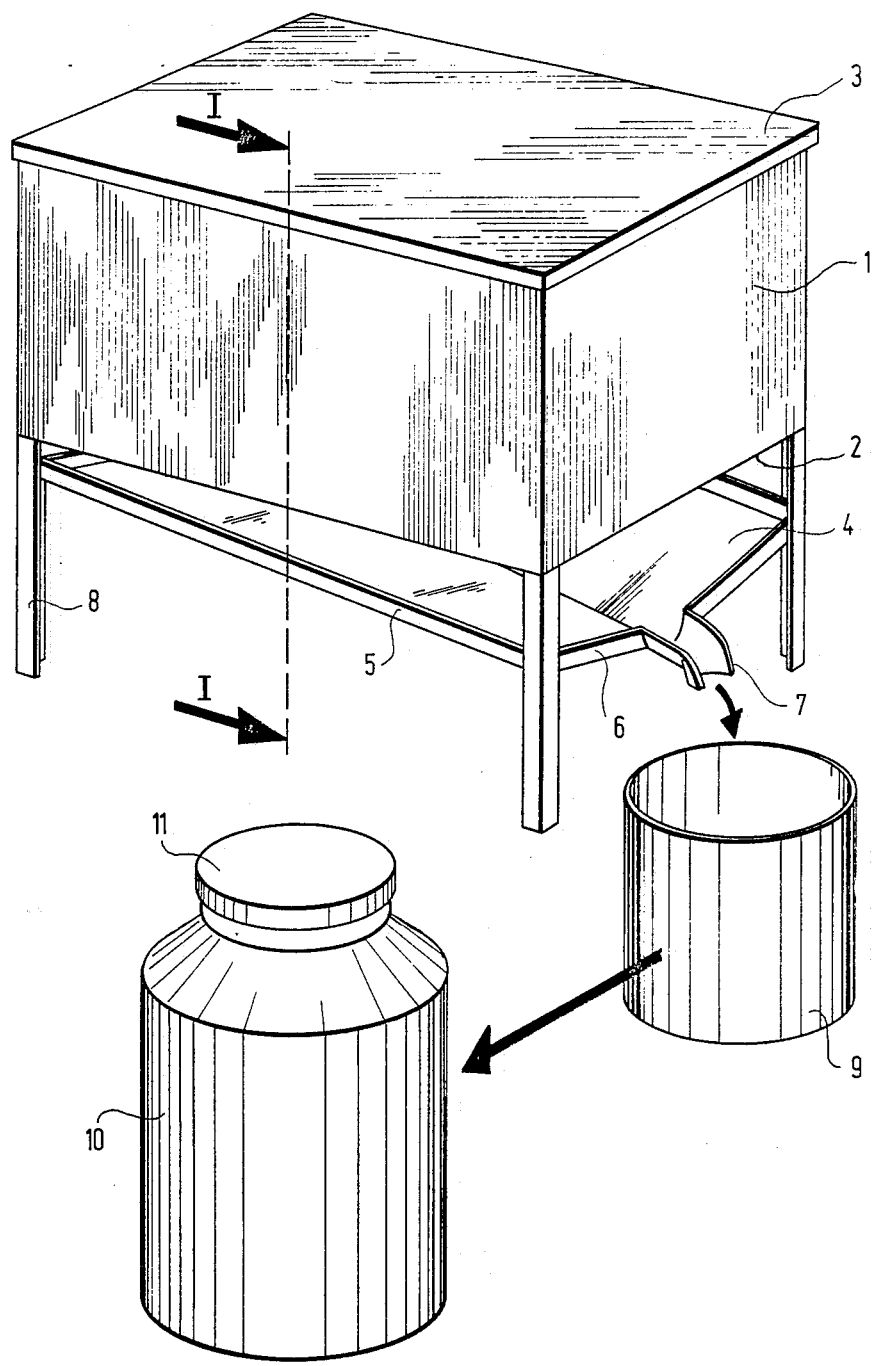
FIG. 1 is a schematic illustration of the apparatus for performing the method.
Figure 2:
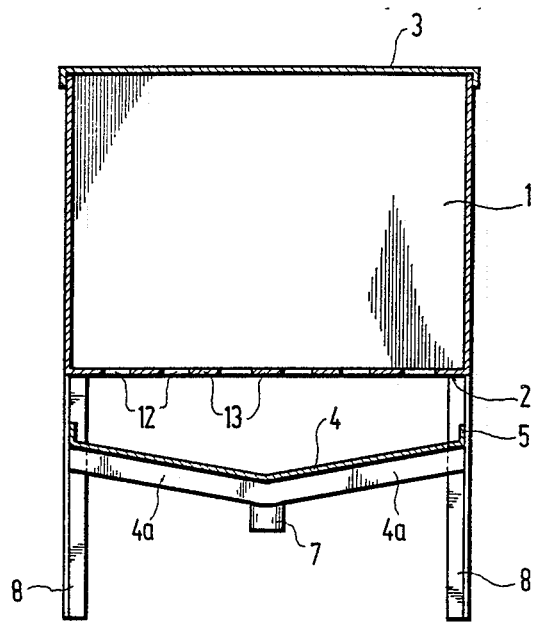
FIG. 2 is a schematic sectional view taken along the line I—I of the container of FIG. 1.

In detail, referring to FIG. 1, the mixture obtained is placed in the cutted state in a container 1 equipped with a hinged lid 3 and a perforated bottom 2, the container preferably being of wood, and left to stand in the container for a period of from several hours to several days; at the beginning, the lid is kept slightly open, and then the lid is kept closed. The ventilation for the fungus and larval material then takes place through the openings in the perforated bottom 2 of the container; the liquid decomposition material, containing larvae, drains out through the openings in the bottom. The container is preferably rectangular and has a bottom of slats, as schematically indicated in FIG. 2; narrow longitudinal gaps 12 extend between the individual slats 13 and through them the liquefied material drains out. The temperature in this phase, as in the other phases, is preferably room temperature, on the order of approximately 15 to 25° C.

During this time, the larvae contained in the fungus material develop extremely strongly, and the larvae, which develop and increase progressively more forcefully have consumed a large part of the fungus substance and excreted again.

The reaction material formed in this process during the above-indicated period of time of several hours to several days, preferably from 12 hours to 2 days, flows through the openings, in particular the longitudinal gaps 12, into a collecting tray 4 located at a distance beneath the container 1 and of equal or greater size; the tray 4 is inclined at the front, in the longitudinal direction along the long edge 5, while the lateral parts of the tray 4a are inclined downward toward the middle of the tray, as can be seen from the cross section of FIG. 2. At the lowermost front point where the two side tray parts 4a meet, which is defined by the front edge 6, there is a drain 7, through which the liquefied material containing larvae is carried into the collecting vessel 9. The container 1 and collecting tray 4 are supported by posts 8.

In the collecting container 9, which is preferably of a corrosion-resistant steel or still more preferably a plastic material that is harmless for foods, the liquid, initially light in color and containing living larvae, stands for a short time, approximately 1 to 6 hours, and then is placed in a holding vessel 10, which is closable in an airtight manner, having a lid 11 that is closed in an airtight manner in this holding vessel 10, it is allowed to stand for a period of from 2 to 5 days, until a dark-brown color and an intense odor have developed, which indicates that the decomposition is complete. At this time, a skin-compatible alcohol is added quickly, while stirring, in a quantity sufficient to kill the larvae; the material in the vessel 10 is thereupon allowed to stand, closed, for from 6 to 15 months and preferably 9 to 12 months. The skin-compatible alcohol is preferably ethanol or isopropanol.

The liquid, dark-brown material obtained during this ripening time of preferably 9 to 12 months exhibits a high and stable content of the desired active components, although it was not possible to analyze or identify them in detail.

The liquid is then separated from the sludge material by conventional methods such as filtering, pressing out or centrifuging. Next, it is made up to suit the desired preparations.

To prepare a hair growth tincture, a hair shampoo or a hair spray, the separated liquid is diluted with a skin-compatible alcohol, fragrances or optionally surface-active agents, as basic shampoo material. The hair tincture has an alcohol content of approximately 15 to 40% by volume, which is the most favorable range for hair sprays as well. In the aqueous hair shampoo composition, the alcohol extract is present in a quantity of approximately 20% by volume, resulting in an alcohol of up to approximately 5% by volume.

The alcohol extracts obtained in the above manner are a dark-brown liquid and are preferably used for regenerating the hair matrix.

To prepare a skin oil or hair oil, the separated fluid is mixed with approximately the same volume of a skin-compatible oil, in particular olive oil or sunflower oil, and heated for a short period of time to 100° C., to drive out alcohol and water. After that, it is allowed to cool, and the oil layer is separated from sludge-like materials by decanting or centrifuging. The oil extract obtained is a yellow, oily liquid that is preferably used for treating the skin and tightening the skin. It is understood that both the alcohol and oil-like extracts may have still other additives, such as preservatives and in particular fragrances, added to them.

The oil extract effects a regeneration and tightening of the skin and in many cases removes spots on the skin.

The alcohol extract terminates hair loss and is effective even with hair loss caused by the side effects of medicines. The hairs become soft, shiny and strong, and even the original hair color is regained. Even for long-existing baldness, the extract causes new hair growth and counteracts increased scalp oiliness and dandruff (seborrhoea). It appears that a total regeneration of the hair and the hair matrix is brought about.

The manner in which the agent acts has not yet been explained. It is assumed that it loosens the hair matrix and deep-cleans the pores. As a result, waste substances are removed, so that the hair roots are not pressed together but instead are given room and are capable of absorbing the active ingredients of the agent. This reactivates the metabolism of the hair matrix and the hair roots, so that the nutrients and growth substances can be effective.

The following examples will further explain the invention.

EXAMPLE 1

60 kg of a fungus mixture of Xerocomus badius and Armillariella were freed of adhering contaminants, and then all the fungi were coarsely cutted. A considerable proportion of the fungus bodies exhibited infestation by larvae of Sciaridae or Mycetophilidae. The pulverized material was placed in a rectangular wood container, which was provided with a hinged lid and a slatted grate having longitudinal gaps from 4 to 8 mm wide. The material was first left to stand for 6 hours with the lid open and then for a further 48 hours with the lid closed, at a temperature of from 15 to 20° C. The fungus-eating larvae developed during this period, and after a further 24 hours had consumed and excreted a great majority of the fungus material. The material obtained was a light-brown liquid and contains a considerable amount of larval material.

The liquid ran through the longitudinal gaps into the collecting tray located beneath them, which was inclined longitudinally and toward the front and had a drain at the lowermost point. The liquid material containing larvae ran out of this drain into a collecting container, where it was left to stand for from 1 to 2 days, until a darker color had appeared. While being stirred, approximately 10 liters of isopropanol was then quickly added at room temperature to the approximately 50 liters of fungus and larval material obtained, which immediately killed the larvae. The material was thoroughly mixed and transferred to a closable container.

In the closable container, the liquid material was left to stand in a climate-controlled room at a temperature of from 20 to 30° C. for approximately 11 months.

Then, the material was placed in a press and pressed out, and the extract was obtained. The extract was a dark-brown liquid with a slight odor having an alcohol content of approximately 5%. It had a high content of active ingredients, as was demonstrated when the preparations obtained from it were used.

EXAMPLE 2

To prepare a hair tincture, the extract was mixed with ethanol as a skin-compatible alcohol, so that a concentration of the alcohol of approximately 20% by volume was obtained.

For use as a regenerating agent for hair growth, approximately 10 to 50 drops of this hair tincture are used daily, rubbed into the scalp and on the hair. The effect begins to be demonstrated after approximately 3 days, and the regrowth of hair begins no later than after a week. Generally, the treatment is continued for 6 weeks. A strong regrowth of hair is demonstrated, which appears virtually in the original color. No side effects were observed.

EXAMPLE 3

To prepare an oil preparation, 2 kg of the extract obtained in example 1 were mixed with approximately 1.8 kg of olive oil and heated for approximately 20 minutes to 100° C. with thorough mixing. The oil layer obtained was decanted and then centrifuged to remove any last contaminants, whereupon a light-yellow oil preparation was obtained.

The skin oil obtained is used for regenerating and tightening aged skin and to eliminate wrinkles. For this purpose, it is rubbed lightly into the skin, and in numerous cases not only tightening of the skin but the removal of skin spots is effected.

I claim:

1. A Method for preparing a biological extract for regenerating the hair and the skin, comprising the following steps:
    (1) a mixture of comminuted receptacles of non-toxic Basidiomycetes and insect larvae that feed on fungi is left to stand for a period of several hours to several days in a container which is perforated at the bottom, and the liquid composition draining off is collected and conducted into a collecting vessel;
    (2) from the collecting vessel, this composition is carried to a vessel that is closable in an airtight manner, in which it is left to stand, closed, for from 2 to 5 days, until a dark-brown color and an intense odor develop;
    (3) a skin-compatible alcohol is thereupon added in a quantity sufficient to kill the larvae;
    (4) the composition is then left to stand, closed, for from 6 to 15 months; and
    (5) then the liquid is separated from the sludge material and mixed with at least one of: a skin-compatible alcohol; a skin-compatible oil.

2. A method as defined by claim 1, wherein the alcohol comprises ethanol or isopropanol.

3. A method as defined by claim 1, wherein the fungus is selected from one or more of the families Agaricales, Boletales, Cantharellaceae.

4. A method as defined by claim 3, wherein the fungus comprise at least one of: Xerocomus badius; Armillariella mellea; Cantharellus cibarius; or mixtures of the foregoing.

5. A method as defined by claim 1, wherein the insect larvae comprise fly larvae.

6. A method as defined by claim 5, wherein the fly larvae comprise at least one of: the families Lycoriidae (Sciaridae); Fungivoridae (Mycetophilidae); or mixtures of the foregoing.

7. A method as defined by claim 1, wherein step (1) includes placing said mixture into a rectangular container of wood having longitudinal gaps on the bottom with a rectangular collecting part inclined toward the drain underneath the container bottom and a drain in the lowermost part of the collecting part.

8. A method as defined by claim 1, wherein steps (1) - (4) are carried out in containers of a material which is inert with respect to the contents therein, and non-reactive with any food products.

9. The method of claim 1, wherein, in step 4, the composition is left to stand from 9 to 12 months.

10. A method for making up a hair tincture, hair shampoo, or hair spray, comprising
    carrying out the method of claim 1; and
    diluting the liquid obtained in step (5) with at least one of: a skin-compatible alcohol; fragrances; surface-active agents as basic shampoo material.

11. A method of making a skin oil comprising
    carrying out the method of claim 1; and
    in step (5), pouring the separated liquid into a skin-compatible oil, to obtain a liquid-oil mixture, and heating said liquid-oil mixture to from about 80° C. to about 100° C.; and
    decanting the oil layer.

12. A method as defined by claim 10, including the step of mixing fragrances with the decanted oil layer.

13. A biological extract for regenerating hair and skin, comprising a liquid mixed with at least one of: a skin-compatible alcohol; a skin-compatible oil, prepared in accordance with the method of claim 1.

14. A hair tincture, hair shampoo or hair spray, which includes a liquid diluted with at least one of: skin-compatible alcohol; fragrances; surface-active agents as basic shampoo material, prepared in accordance with the method of claim 10.

15. A skin oil comprising a separated liquid mixed with a skin-compatible oil which has been heated, and decanted, made in accordance with the method of claim 11.

16. An apparatus for carrying out the method as defined by claim 1 comprising a container (1) having a hinged lid (3) and a perforated bottom (2);

a collecting tray (4) attached beneath the bottom (2), the collecting tray being inclined to the front with respect to the container (1) and inclined downward from the long edges (5) toward the middle of the collecting tray and having a drain (7) at the lowermost point, a collecting vessel (9) positioned to receive liquid from said drain; and a holding vessel (10) closable in an airtight manner receiving liquids from said collecting vessel.

17. An apparatus as defined by claim 16, wherein the container (1) and the collecting tray (4) are made from wood.

18. An apparatus as defined by claim 16, wherein the perforated bottom (2) comprises a slatted grate having longitudinal slats (13) and gaps (12) between the slats.

* * * * *